United States Patent
Hu et al.

(10) Patent No.: US 10,010,883 B2
(45) Date of Patent: Jul. 3, 2018

(54) DETERMINISTIC LATERAL DISPLACEMENT ARRAYS

(71) Applicant: INTERNATIONAL BUSINESS MACHINES CORPORATION, Armonk, NY (US)

(72) Inventors: Huan Hu, Yorktown Heights, NY (US); Sung Cheol Kim, White Plains, NY (US); Joshua T. Smith, Hudson, NY (US); Benjamin H. Wunsch, Mt. Kisco, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 3 days.

(21) Appl. No.: 15/270,514

(22) Filed: Sep. 20, 2016

(65) Prior Publication Data
US 2018/0078939 A1    Mar. 22, 2018

(51) Int. Cl.
*B01L 3/00* (2006.01)
*G01N 33/00* (2006.01)
*G01N 15/06* (2006.01)
*G01N 33/48* (2006.01)
*B03B 5/48* (2006.01)

(52) U.S. Cl.
CPC .......... *B01L 3/502761* (2013.01); *B03B 5/48* (2013.01); *B01L 2200/0636* (2013.01); *B01L 2200/0652* (2013.01); *B01L 2300/0816* (2013.01)

(58) Field of Classification Search
CPC .......... B01L 3/00; G01N 33/00; G01N 15/06; G01N 33/48
USPC ......... 422/68.1, 502, 503, 504; 436/43, 174, 436/180
See application file for complete search history.

(56) References Cited

U.S. PATENT DOCUMENTS

| | | | |
|---|---|---|---|
| 5,427,663 A | 6/1995 | Austin et al. | |
| 7,150,812 B2 | 12/2006 | Huang et al. | |
| 8,186,913 B2 | 5/2012 | Toner et al. | |
| 8,263,023 B2 | 9/2012 | Le Vot et al. | |
| 8,807,879 B2 | 8/2014 | Toner et al. | |
| 9,347,595 B2 | 5/2016 | Toner et al. | |
| 2014/0315303 A1* | 10/2014 | Huang | B01L 3/502 435/366 |
| 2015/0362413 A1* | 12/2015 | Zhang | B01D 21/00 210/801 |
| 2016/0047735 A1* | 2/2016 | Grisham | G01N 15/1484 435/7.1 |

(Continued)

*Primary Examiner* — Brian J. Sines
(74) *Attorney, Agent, or Firm* — Cantor Colburn LLP; Vazken Alexanian

(57) ABSTRACT

A deterministic lateral displacement array that includes a channel, within a substrate, having a first sidewall, a second sidewall, and a channel length. A condenser portion that includes an entry port and an exit port. A first array of pillars is disposed between the entry port and the exit port of the condenser portion along the channel length, the first array of pillars operative to drive a first material particle and a second material particle towards the first sidewall of the channel. A separator portion that includes an entry port and an exit port, and a second array of pillars disposed between the entry port and the exit port of the separator portion along the channel length, the pillars operative to drive the first material particle towards the second sidewall of the channel.

5 Claims, 9 Drawing Sheets

(56) References Cited

U.S. PATENT DOCUMENTS

| | | |
|---|---|---|
| 2016/0115520 A1* | 4/2016 | Krishnamurthy ........ C12Q 1/04 |
| | | 435/30 |
| 2016/0123857 A1* | 5/2016 | Kapur .................. G01N 1/4077 |
| | | 435/2 |
| 2016/0139012 A1* | 5/2016 | D'Silva .............. G01N 33/5094 |
| | | 424/93.7 |
| 2016/0144361 A1 | 5/2016 | Astier et al. |
| 2016/0144405 A1 | 5/2016 | Astier et al. |
| 2016/0144406 A1 | 5/2016 | Astier et al. |
| 2016/0146717 A1 | 5/2016 | Astier et al. |
| 2016/0146718 A1 | 5/2016 | Astier et al. |
| 2016/0146778 A1 | 5/2016 | Astier et al. |
| 2016/0168539 A1 | 6/2016 | Civin et al. |
| 2017/0248508 A1* | 8/2017 | Ward ................. G01N 15/1056 |

* cited by examiner

DETERMINISTIC LATERAL DISPLACEMENT ARRAYS

BACKGROUND

The present invention relates in general to deterministic lateral displacement arrays and, more specifically, to using deterministic lateral displacement arrays for particle separation.

In microfluidic devices, the fluid behaves according to the laws of laminar flow, which has high viscosity and no inertia motion. Due to the lack of inertia motion, the flow has time reversibility that makes the mixing of two parallel flow streams challenging on a practical timescale. Adjacent flow streams can be used to compress and "sculpt" a liquid stream without diluting the contents (e.g. particles, analytes) of the stream itself. This method is called hydrodynamic focusing and has been used to generate concentrated "jets" of fluid flow, with narrow cross-sections, for microfluidic applications such as emulsion formation and localized sample feeding. This method has the ability to concentrate a stream of fluid or sample, thus reducing diffusion effects, increasing the local density of analytes, and allowing controlled spatial placement of the stream within a fluidic channel.

SUMMARY

According to an embodiment of the present invention, a method of forming a deterministic lateral displacement array is provided. The method includes forming a channel, within a substrate, having a first sidewall, a second sidewall, and a channel length. The channel includes a condenser portion and a separator portion. The condenser portion includes an entry port and an exit port. The method includes forming a first array of pillars disposed between the entry port and the exit port of the condenser portion along the channel length, the first array of pillars operative to drive a first material particle and a second material particle towards the first sidewall of the channel and the separator portion includes an entry port and exit port, the entry port of the separator portion arranged with the exit portion of the condenser portion such that the first material particle and the second material particle flow from the exit port of the condenser portion into the entry port of the separator portion. Forming a second array of pillars disposed between the entry port and the exit port of the separator portion along the channel length, the pillars operative to drive the first material particle towards the second sidewall of the channel.

According another embodiment of the present invention, a deterministic lateral displacement array is provided. The deterministic lateral displacement array includes a channel, within a substrate, having a first sidewall, a second sidewall, and a channel length. A condenser portion that includes an entry port and an exit port. A first array of pillars disposed between the entry port and the exit port of the condenser portion along the channel length, the first array of pillars operative to drive a first material particle and a second material particle towards the first sidewall of the channel. A separator portion that includes an entry port and an exit port, the entry port of the separator portion arranged with the exit port of the condenser portion such that the first material particle and the second material particle flow from the exit port of the condenser portion into the entry port of the separator portion and a second array of pillars disposed between the entry port and the exit port of the separator portion along the channel length, the pillars operative to drive the first material particle towards the second sidewall of the channel.

According to another embodiment of the present invention, a method for forming a deterministic lateral displacement array is provided. The method includes forming a channel, within a substrate, having a first sidewall, a second sidewall, and a channel length. The channel includes a condenser portion and a separator portion. The condenser portion includes an entry port and an exit port. The method includes forming a first array of pillars disposed between the entry port and the exit port of the condenser portion along the channel length, the first array of pillars operative to drive a first material particle and a second material particle towards a center of the channel equidistance from the first sidewall and the second sidewall and the separator portion includes an entry port and exit port, the entry port of the separator portion arranged with the exit portion of the condenser portion such that the first material particle and the second material particle flow from the exit port of the condenser portion into the entry port of the separator portion. Forming a second array of pillars disposed between the entry port and the exit port of the separator portion along the channel length, the pillars operative to drive the first material particle towards both the first sidewall and the second sidewall.

According to anther embodiment of the present invention, a deterministic lateral displacement array is provided. The deterministic lateral displacement array includes a channel, within a substrate, having a first sidewall, a second sidewall, and a channel length. A condenser portion that includes an entry port and an exit port. A first array of pillars disposed between the entry port and the exit port of the condenser portion along the channel length, the first array of pillars operative to drive a first material particle and a second material particle towards a center of the channel equidistance from the first sidewall and the second sidewall. A separator portion that includes an entry port and an exit port, the entry port of the separator portion arranged with the exit port of the condenser portion such that the first material particle and the second material particle flow from the exit port of the condenser portion into the entry port of the separator portion and a second array of pillars disposed between the entry port and the exit port of the separator portion along the channel length, the pillars operative to drive the first material particle towards both the first sidewall and the second sidewall.

BRIEF DESCRIPTION OF THE DRAWINGS

The subject matter of the present invention is particularly pointed out and distinctly defined in the claims at the conclusion of the specification. The foregoing and other features and advantages are apparent from the following detailed description taken in conjunction with the accompanying drawings in which:

DETAILED DESCRIPTION

Deterministic lateral displacement (DLD) devices are utilized to separate particles within a fluid. The embodiments described herein focus particle concentrations within a channel and then separate larger particles from smaller particles. Microfluidic devices often utilize hydrodynamic focusing to generate a concentrated jet of fluid flow. However, the focusing jet uses extra channels with specific pressure controls. The focusing jets involve additional complexity for tuning and careful control on the focusing process. The embodiments described herein focus particles within a fluid flow without extra side channels or electric fields.

A deterministic lateral displacement arrays is provided. Embodiments described herein include a channel within a substrate that contains a condenser portion and a separator portion. The channel length in both the condenser and separator portions has a first and second sidewall. In the condenser portion, there is an entry and exit port that receives a fluid containing two particles, a large particle and a small particle. Within the channel of the condenser portion is a first array of pillars that are disposed between the entry and exit port along the length of the channel. The arrangement of the first array of pillars in the condenser portion drives both the large particles and the small particles towards the first sidewall of the condenser portion. In the separator portion, there is an entry and exit port capable of receiving the fluid. Within the channel of the separator portion is a second array of pillars that are disposed between the entry and exit port along the length of the channel within the separator. The arrangement of the second array of pillars in the separator portion drives the large particle towards the second side wall of the separator portion.

Figure 1:
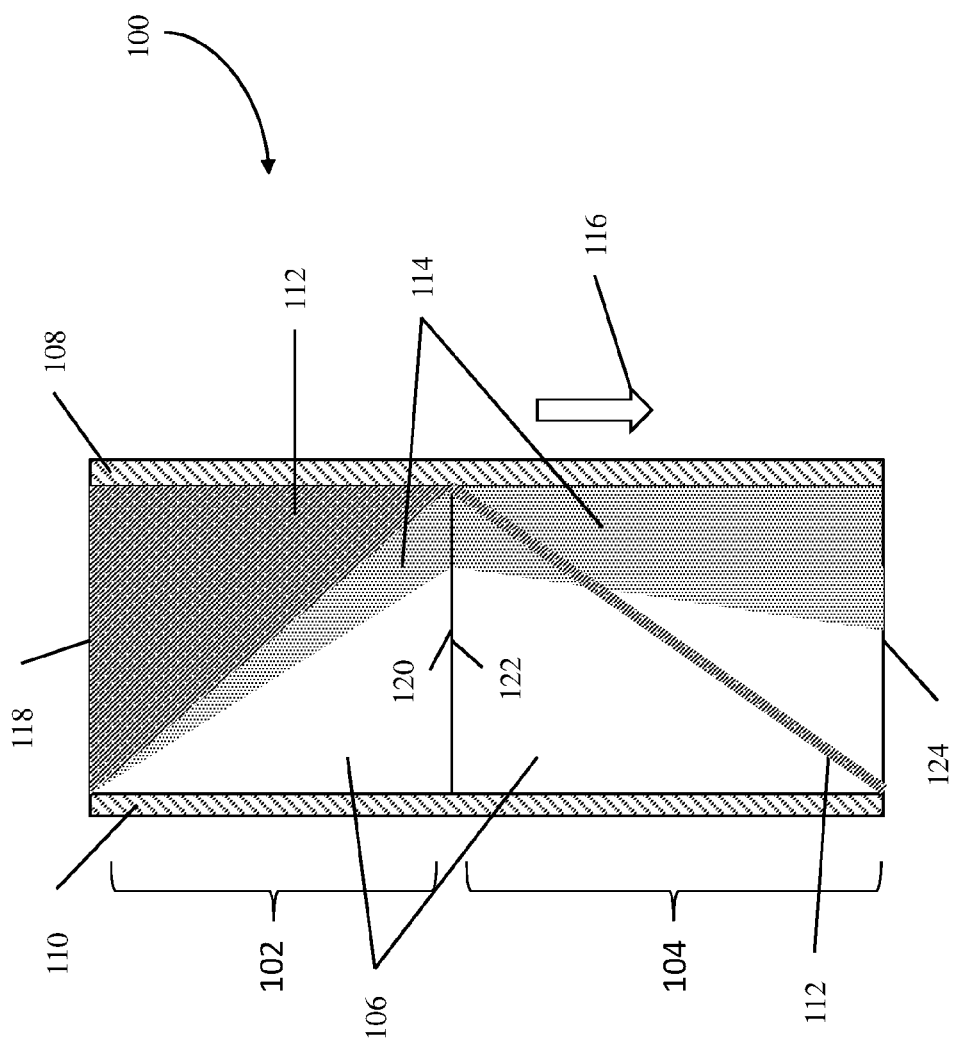
FIG. 1 illustrates a top down partially cut-away view of a deterministic lateral displacement array.

FIG. 1 illustrates a top down partially cut-away view of an exemplary embodiment of a deterministic lateral displacement array. The deterministic lateral displacement array 100 includes a condenser portion (condenser) 102 and a separator portion (separator) 104. Each of the condenser 102 and separator 104 includes a channel 106. Disposed within the channel 106 are a first patterned array 203 (of FIG. 2) of pillars 204 (of FIG. 2) and a second patterned array 503 (of FIG. 5) of pillars 504 (of FIG. 5). Each of the condenser 102 and separator 104 includes a first sidewall 108 and a second sidewall 110. The condenser 102 includes an entry port 118 and an exit port 120. The separator 104 includes an entry port 122, which abuts to the exit port 120 of the condenser, and an exit port 124.

The deterministic lateral displacement array 100 is operative to receive a fluid. In the illustrative example, the fluid includes a first material 112 and a second material 114 that are suspended in the fluid. The first material 112 has a first particle size and the second material 114 has a second particle size. In the illustrated exemplary embodiment, the first particle size is larger than the second particle size. While the illustrative example shows a fluid with two materials, any number of materials within a fluid can be passed into the deterministic lateral displacement array 100. The flow direction 116 of the fluid is shown to be substantially axial along the length of the channel.

In operation, the condenser 102 first concentrates the first and second particles of the first 112 and second 114 material into a focused jet close to the first sidewall 108. The separator 104 then separates the larger particles from the smaller particles by forcing the larger particles of the first material 112 towards the second sidewall 110. The smaller particles of the second material 114 generally follow the fluid flow direction 116.

Figure 2:
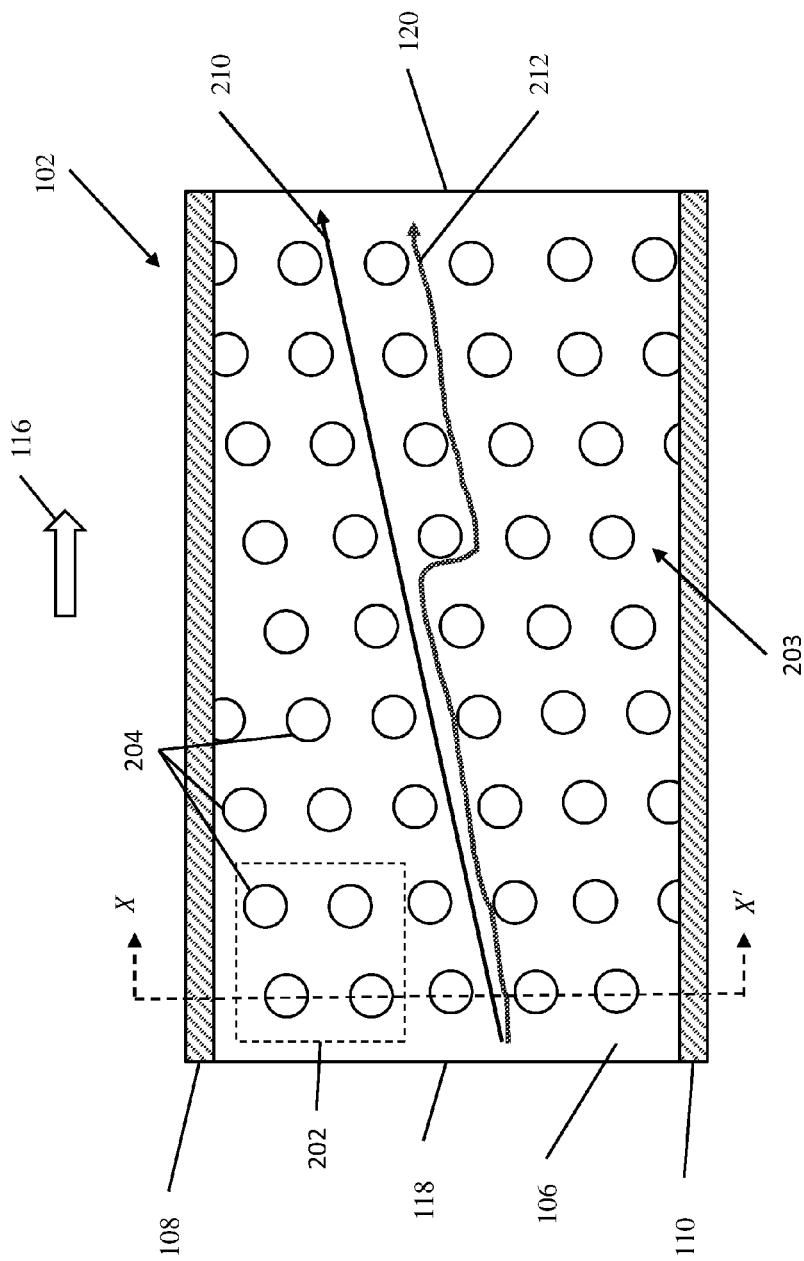
FIG. 2 illustrates a top down view of a first portion of the deterministic lateral displacement array.

FIG. 2 illustrates top down view of the first portion of the deterministic lateral displacement array according to one or more embodiments. The first portion of the deterministic lateral displacement array is the condenser 102. The condenser 102 includes a channel 106, a first sidewall 108 and second sidewall 110. Disposed within the channel 106, is an array 203 of pillars 204. The condenser 102 includes an input port 118 and an output port 120.

The pillars 204 are disposed on the channel 106 and arranged in a patterned array 203. The array 203 of pillars 204 are arranged or patterned with a desired size, shape, and relative position to concentrate the large particles at the first sidewall 108. The large particles have an over-critical diameter, as it relates to the array 203, and migrate towards the first sidewall 108. When the large particles traverse the condenser 102, the large particles bump through the off-shifted pillars 204 and migrate along a bumping direction 210. The smaller particles do not have an over-critical diameter, and, thus, migrate in a zig-zag shaped path 212 along the pillar array 203.

Figure 3:
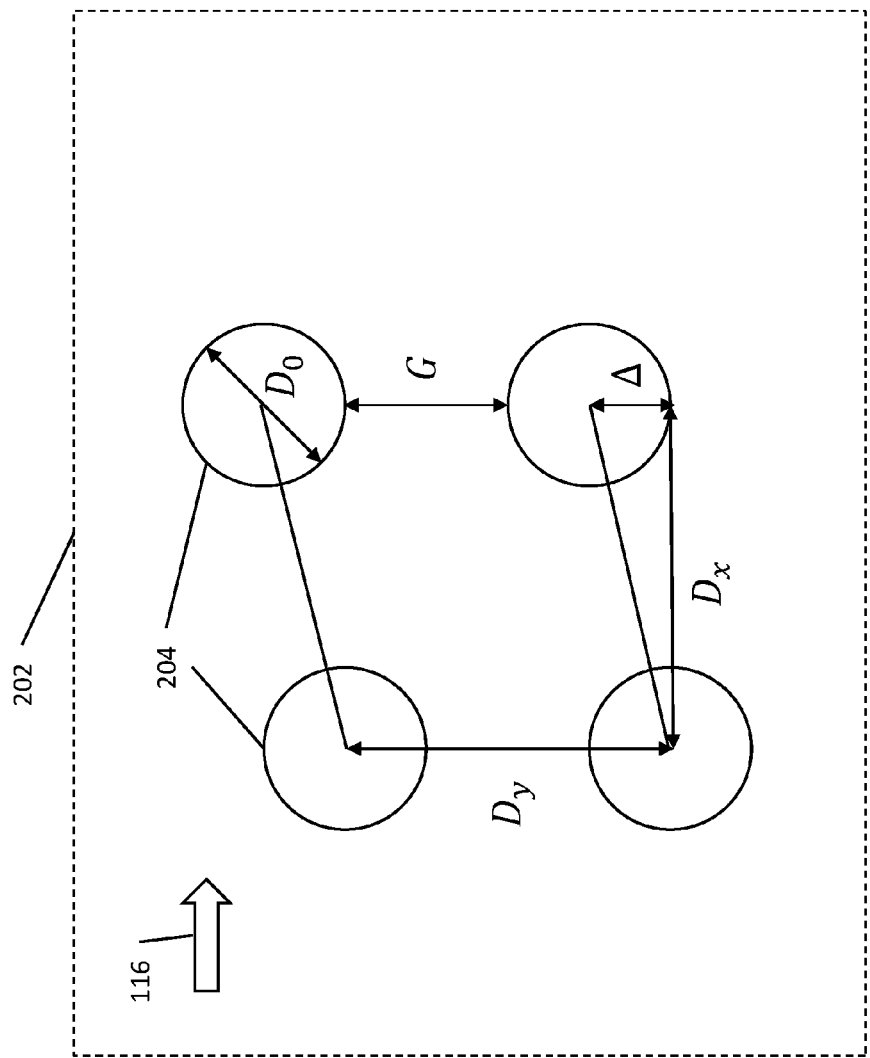
FIG. 3 illustrates a top down view of a portion of the array of four pillars in a condenser that includes four pillars.

FIG. 3 illustrates a top down view of a portion of the array 203 of pillars 204 in the condenser 102 that includes four pillars 202. The other pillars in the array 203 in the condenser 102 are sized and shaped in a similar arrangement as the four pillars 202. The four pillars 202 include the following geometric parameters: a $D_0$, a $D_y$, a $D_x$, a G, and a $\Delta$. The $D_0$ is a diameter of a pillar 204. The $D_x$ is the center to center distance between pillar centers substantially parallel to the flow direction 116. The $D_y$ is the center to center distance between pillar centers substantially perpendicular to the flow direction 116. The G is a gap distance between pillars, which is the distance between the outer surfaces of two pillars. And the $\Delta$ is the off-set displacement of a pillar with respect to another pillar in the flow direction 116. The four pillars 202 illustrate a portion of the array of pillars. In one or more embodiments, the geometric parameters of the four pillars 202 are uniform across the array of pillars within the condenser 102. In one or more embodiments, the pillars 204 in the array 203 can follow a similar size, shape, and arrangement as the four pillars 202 within the condenser 102.

Figure 4:
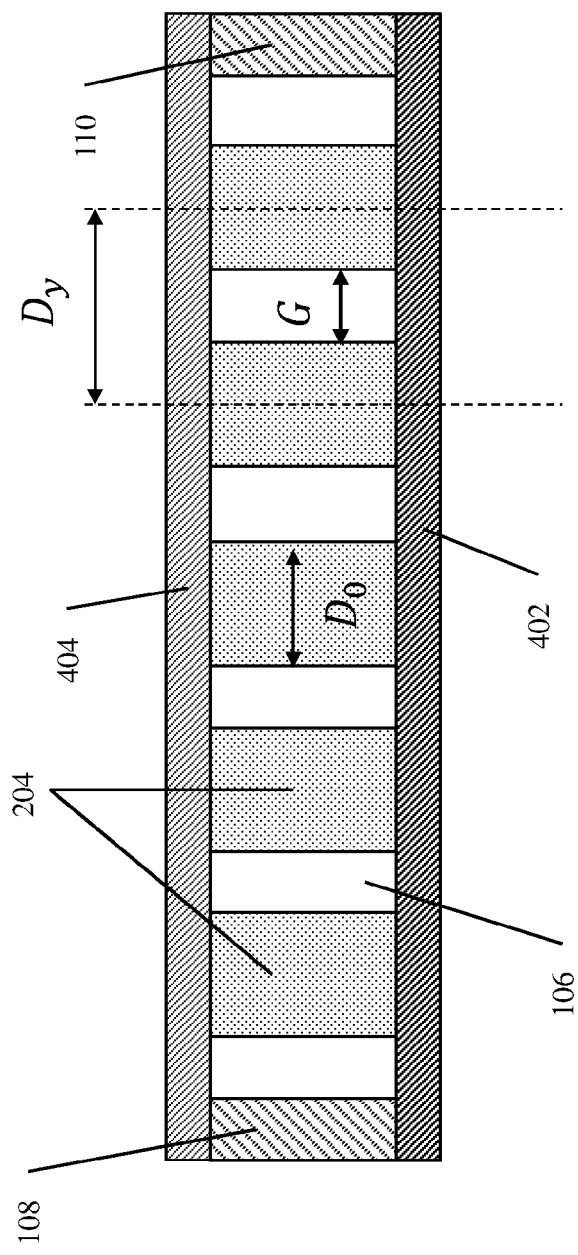
FIG. 4 illustrates a cross-sectional view, along the line X-X' of FIG. 2.

FIG. 4 illustrates a cross-sectional view along the line X-X' of FIG. 2 according to the illustrated exemplary embodiment. The cross-sectional view includes a floor 402, a cover 404, the first sidewall 108, and the second sidewall 110 of the deterministic lateral displacement array 100. Disposed on the lower wall 402 are the pillars 204 with the geometric parameters of $D_0$ and G. $D_0$ is the diameter of each of the pillars 204 and G is the gap distance between the outer surfaces of the pillars substantially perpendicular to the flow direction 116. $D_y$ is the center to center distance between pillar centers substantially perpendicular to the flow direction 116. The pillars 204 are shown within the channel 106. The cover 404 is not shown in FIG. 2.

Figure 5:
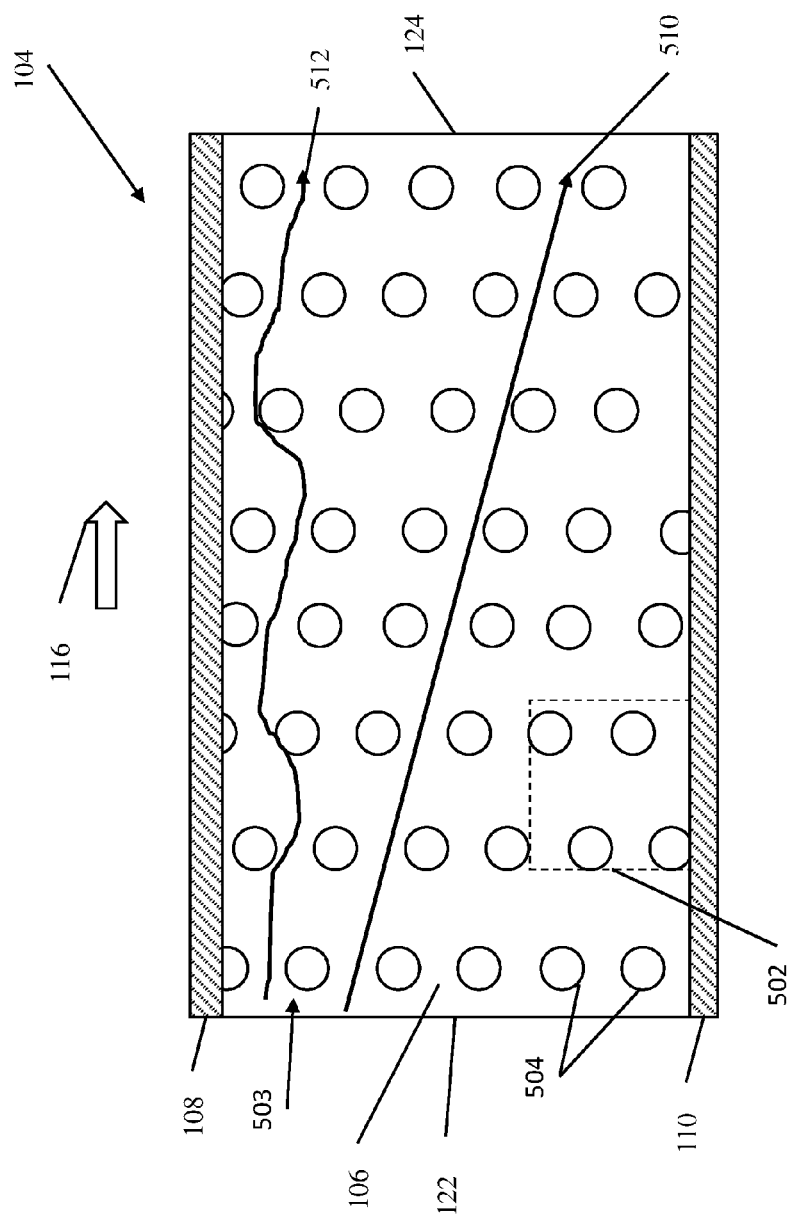
FIG. 5 illustrates a top down view of an example of second portion of the deterministic lateral displacement array.

FIG. 5 illustrates a top down view of an example of the second portion of the deterministic lateral displacement array. The second portion of the deterministic lateral displacement array is the separator 104. The separator 104 includes a channel 106, a first sidewall 108, and second sidewall 110. Disposed within the channel 106, is an array 503 of pillars 504. The separator 104 includes an input port 122 and an output port 124.

The pillars 504 are disposed on the channel 106 and arranged in a patterned array 503. The pillars 504 are arranged or patterned with a desired size, shape, and relative position to concentrate the large particles at the second sidewall 110. The large particles have an over-critical diameter. Because the large particles have the larger or over-critical diameter, when fed through the condenser 102, the large particles bump through the off-shifted pillars 504 and migrate along a bumping direction 510 towards the second sidewall 110. The smaller particles do not have an over-critical diameter, and, thus, migrate in a zig-zag shaped direction 512 along the pillar array 503. Due to the geometric parameters of the separator, the smaller particles generally follow the fluid flow direction 116.

Figure 6:
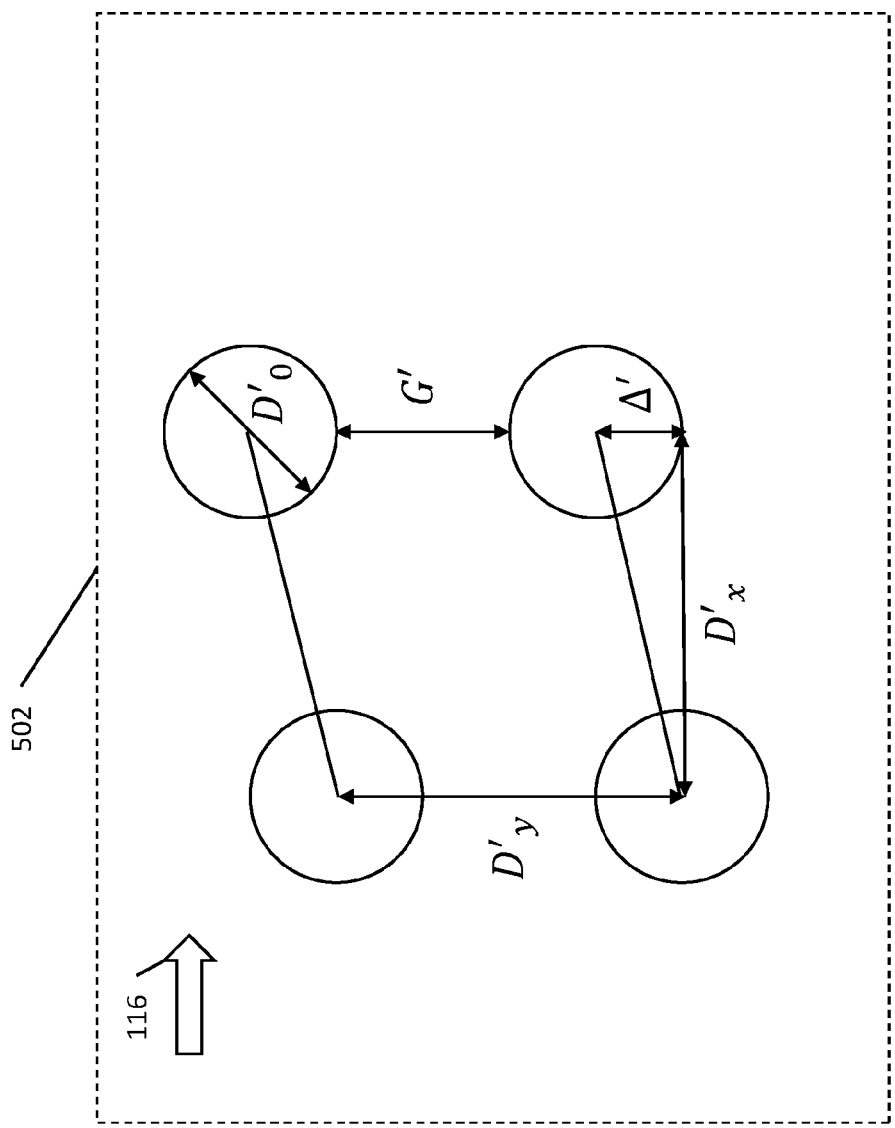
FIG. 6 illustrates a top down view of a portion of the array of pillars in a separator that includes four pillars.

FIG. 6 illustrates a top down view of a portion of the array 503 of pillars 504 in the separator 104 that includes four pillars 502. The four pillars 502 include the following geometric parameters: a $D_0'$, a $D_y'$, a $D_x'$, a G', and a Δ'. The pillars 204 in the condenser 102 have geometric parameters that can be different from the geometric parameters of the pillars 504 in the separator 104. The $D'_0$ is a diameter of a pillar 504. The $D_x'$ is the center to center distance between pillar centers substantially parallel to the flow direction 116. The $D_y'$ is the center to center distance between pillar centers substantially perpendicular to the flow direction 116. The G' is a gap distance between pillars, which is the distance between the outer surfaces of two pillars. And the Δ' is the off-set displacement of a pillar with respect to another pillar in the flow direction 116. Δ' can be referred to as the row-shift displacement. The four pillars 502 illustrate a portion of the array 503 of pillars 504. In one or more embodiments, the four pillars 502 follow a similar size, shape, and arrangement as the array 503 of pillars 504 within the separator 104.

The condenser 102 is utilized for focusing the larger and smaller particles with a maximum asymmetric penetrability. The separator 104 is utilized for separating the particles by the size difference with an increased migration angle difference. The pillars 204, 504 within the pillar array 203, 503 are constructed within a fluidic channel 106 in which a fluid flow follows axially along the direction of the channel (i.e. the flow direction 116), while a lattice translation vector follows along at an angle set by the geometric parameters of the pillars 204, 504 within the pillar array 203, 503. This angle is referred to as the bumping angle. Should a particle be deflected by the array, the angle of the particle follows the bumping angle. If the particle is deflected by less than the bumping angle, it can be referred to as the migration angle. If a particle follows the flow stream in the channel 106, then its motion is called a zig-zag mode and its migration angle is effectively zero.

Figure 7:
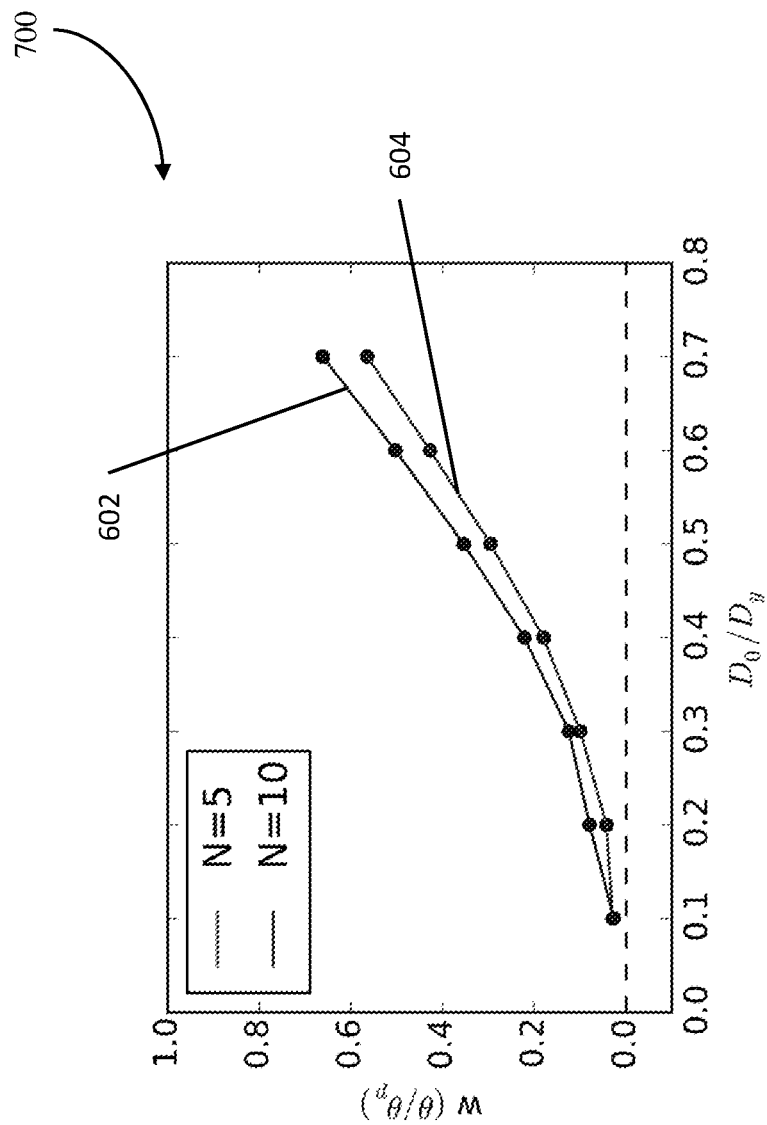
FIG. 7 illustrates a graph showing the predicted migration angle of a particle in an array with pillar diameter and pillar center distance that is substantially perpendicular to the flow direction.

FIG. 7 illustrates a graph 700 showing the predicted migration angle of a particle in an array with pillar diameter ($D_0$) and pillar center distance ($D_y$) which is perpendicular to the flow direction 116. The x-axis shows the ratio of pillar diameter ($D_0$) to pillar center distance ($D_y$), i.e., $D_0/D_y$. This ratio can also be referred to as the migration ratio. The y-axis shows the degree, W, by which two particles diverge. The two particles are referred to as the large particle and small particle. $\theta_p$ is the migration angle of the bumping particle (i.e. the large particle). θ is the migration angle of the zig-zag particle (i.e. the small particle).

N is the row shift ratio which shows the ratio of the pillar center distance ($D_y$) to the row-shift displacement (Δ), i.e. $D_y/\Delta$. In the illustrative example, the row shift ratios are N=5 and N=10. The graph line for N=5 is shown as 602 and the graph line for N=10 is shown as 604. As the $D_0/D_y$ ratio tends towards one, the ratio between the two migration angles (θ and $\theta_p$) tends to one. As the $D_0/D_y$ ratio tends to one, the migration angles are close and the two particles are moving at the similar angle as seen in the condenser 104. In one or more embodiments, for a condenser 102, the $D_0/D_y$ is in the range of 0.6-0.7 and for a separator 104, the $D_0/D_y$ is in the range of 0.3-0.4. The separator 104 has a lower ratio of migration angles because it is diverting the particles away from the narrow particle stream created by the condenser 102. By changing the geometric parameters in the pillar array, the zig-zag motion of the smaller particle can be changed from a zero value to a non-zero value thus diverting the particle out of the normal flow stream of the fluid.

In the exemplary case of N=5, the result of graph 700 can be fitted with the function y=1.2116x^2.0748 and in the case of N=10, the results of graph 700 can be fitted with the function y=1.2068x^1.7508. Therefore, once the ratio $D_0/D_y$ is determined, the migration ratio between the large particle and the small particle is determined. After the migration ratio is determined, a migration angle for the small particles is calculated.

The geometric parameters of the pillars 204 in the array 203 in the condenser 102 can be calculated according to the following example. Assuming the large particle diameter is 500 nm and the small particle is 300 nm and N=5 in the array 203, the calculated target diameter, $D_c$, is 400 nm. $D_c$ is determined utilizing the formula $D_c$=1.4G(1/N)^0.48. From this formula, the gap G is determined to be 870 nm.

In condenser 102, a $D_0/D_y$ ratio is chosen between 0.6-0.7 to make the migration angle of large and small particles close to each other. In the example, if 0.6 is chosen as the value for the $D_0/D_y$ ratio and G=870 nm, utilizing the formula ($D_y=D_0+G$), the calculated values for the following parameters are $D_y$=1550 nm and $D_0$=930 nm. From these calculated values, the migration angles can be calculated utilizing a fitting function. The bumping angle is ARCTAN (1/N)=11.31 degrees and the migration ratio is 0.42 from the fitting function (y=1.2116x^2.0748). The migration angle of the small particle is 4.75 degrees. With a channel that is 50 μm wide and 600 μm long, the particles are focused as desired.

In the illustrative example, the graph 700 shows that as the ratio between the pillar diameter and the center to center distance of the pillars, the asymmetric permeability increases. The flow is focused more toward the first sidewall 108 of the channel as propagating along the pressure gradient direction (i.e. the flow direction 116). The focusing is controlled by the geometric parameters of the pillar array and the off-shift displacement (N).

Figure 8:
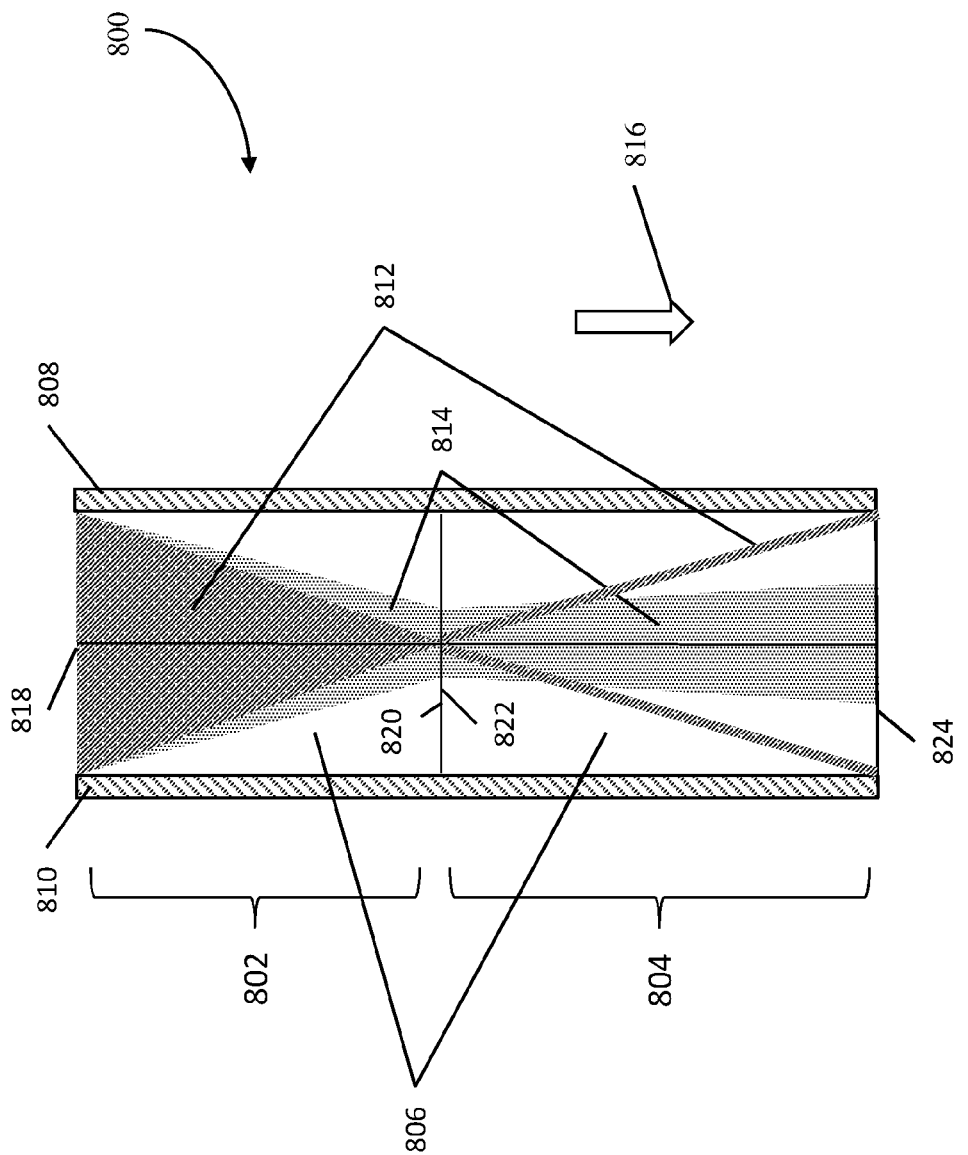
FIG. 8 illustrates a top down partially cut-away view of an alternative exemplary embodiment of a deterministic lateral displacement array.

FIG. 8 illustrates a top down view of an alternate exemplary embodiment of a deterministic lateral displacement array. The deterministic lateral displacement array 800 includes a condenser 802 and a separator 804. Each of the condenser 802 and separator 804 includes a channel 806. Each of the condenser 802 and separator 804 includes a first sidewall 808 and a second sidewall 810. The condenser 802 includes an entry port 818 and an exit port 820. The separator 804 includes an entry port 822, which abuts to the exit port 820 of the condenser, and an exit port 824.

Within the channel 806 are a first and second patterned array of pillars that are similar to the first and second patterned array of pillars in FIG. 2 and FIG. 5. The pillars in the array of the condenser 802 have geometric parameters as described above in FIG. 3 and FIG. 6. The pillars in the array have a desired size, shape, and relative position that concentrate the large particles and the small particles to the center of the channel 806 roughly equidistance between the first 808 and second 810 sidewalls. The pillars in array of the separator have geometric parameters as described above in FIG. 3 and FIG. 6. The pillars in the array have a size, shape, and relative position that concentrate the larger particles of the first material 812 to each of the first sidewall 808 and the second sidewall 810. The size, shape, and relative position of the pillars in the array cause the smaller particles to generally follow the fluid flow path 816.

The deterministic lateral displacement array 800 is operative to receive a fluid. In the illustrative example, the fluid includes a first material 812 and a second material 814. The first material 812 has particles of a first particle size and the second material 814 has particles of a second particle size. The first particle size is larger than the second particle size. While the illustrative example shows a fluid with two materials, any number of materials within a fluid can be passed into the deterministic lateral displacement array 800. The flow direction 816 of the fluid is shown to be axial along the direction of the channel 806.

The condenser 802 first concentrates the first and second particles of the first 812 and second 814 material into a focused jet close to the center of the channel 806 roughly equidistance between the first 808 and second 810 sidewalls. The separator 804 then separates out the larger particles by forcing the larger particles of the first material 812 to each of the first sidewall 808 and the second sidewall 810. The smaller particles of the second material 814 are not forced to either of the sidewalls.

Figure 9:
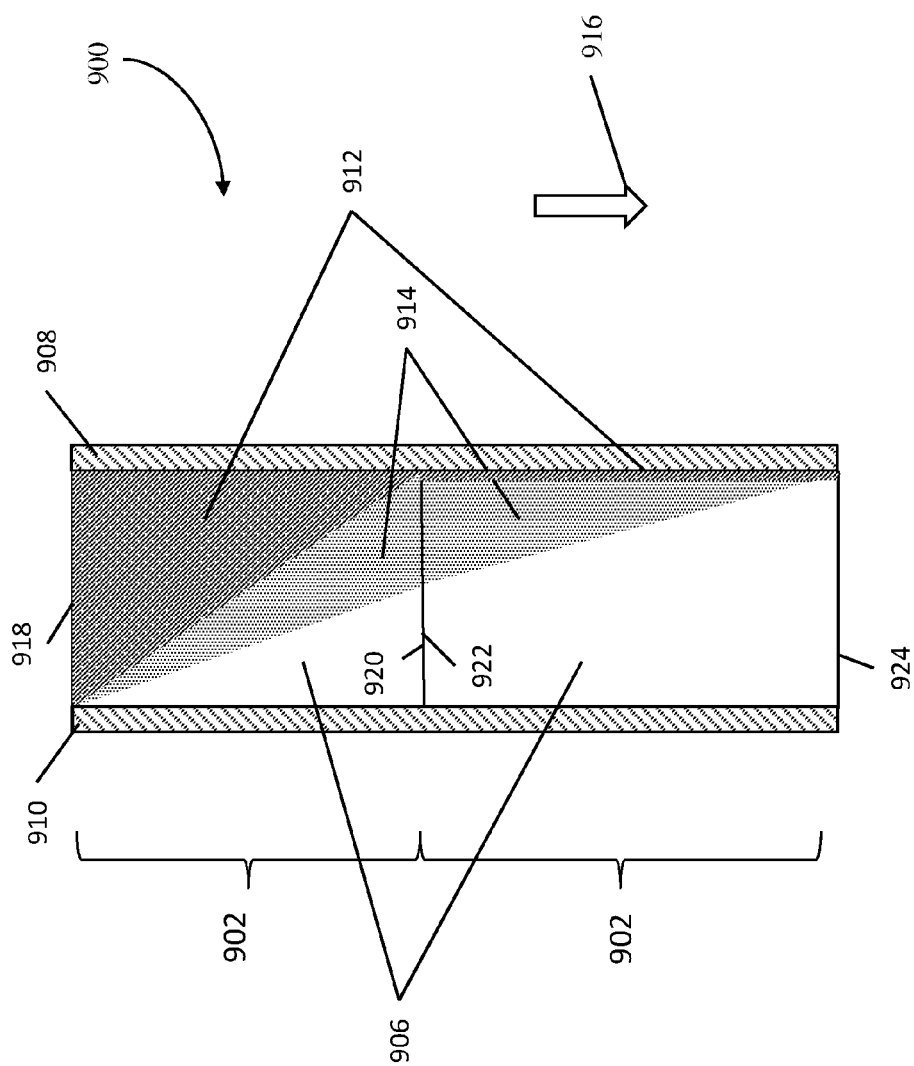
FIG. 9 illustrates a top down partially cut-away view of a particle condenser according to one or more embodiments of the present invention.

FIG. 9 illustrates a top down view of an exemplary embodiment of a particle condenser. The particle condenser 900 includes a first condenser 902 and a second condenser 904. Each of the first condenser 902 and the second condenser 904 includes a channel 906. Within the channel 906 are a first and a second patterned array of pillars which are similar to the first patterned array 203 of FIG. 2. Each of the first condenser 902 and the second condenser 904 includes a first sidewall 908 and a second sidewall 910. The first condenser 902 includes an entry port 918 and an exit port 920. The second condenser 904 includes an entry port 922, which abuts to the exit port 920 of the first condenser 902, and an exit port 924.

The particle condenser 900 is operative to receive a fluid. In the illustrative example, the fluid includes a first material 912 and a second material 914. The first material 912 has a first particle size and the second material 914 has a second particle size. In one or more embodiments, the first particle size is larger than the second particle size. While the illustrative example shows a fluid with two materials, more than two materials within a fluid can be passed into the particle condenser 900. The flow direction 916 of the fluid is shown to be axial along the direction of the channel 906.

The first condenser 902 first concentrates the first and second particles of the first 912 and second 914 material into a focused jet close to the first sidewall 908. The second condenser 904 then focuses the first particles of the first material 912 as well as the second particles of the second material 914 to even closer to the first sidewall 908. In one or more embodiment, a separator can be placed at the exit port 924 of this first 902 and second 904 condenser combination.

The deterministic lateral displacement arrays 100, 800, and the particle condenser 900 can be constructed on silicon wafers, patterned by, for example, photolithographic patterning and etching processes. In the illustrated example, features such as pillars are etched by using an etching process to obtain nearly vertical sidewalls. Devices can be coated with a fluorosilicate vapor and sealed by glass coverslips coated with polydimethylsiloxane (PDMS) silicone on the sealing surface. The deterministic lateral displacement arrays 100, 800, and the particle condenser 900 can be placed into a Plexiglas chuck for loading and application of pressures.

The deterministic lateral displacement arrays 100, 800, and particle condenser 900 can be micro/Nano-fabricated. Microfabrication techniques can be selected from, for example, techniques conventionally used for silicon-based integrated circuit fabrication, embossing, casting, injection molding, and so on. Examples of suitable fabrication techniques include photolithography, electron beam lithography, imprint lithography, reactive ion etching, wet etch, laser ablation, embossing, casting, injection molding, and other techniques. The deterministic lateral displacement arrays 100, 800, and particle condenser 900 can be fabricated from materials that are compatible with the conditions present in the particular application of interest. Such conditions include, but are not limited to, pH, temperature, application of organic solvents, ionic strength, pressure, application of electric fields, surface charge, sticking properties, surface treatment, surface functionalization, and bio-compatibility. The materials of the device are also chosen for their optical properties, mechanical properties, and for their inertness to components of the application to be carried out in the device. Such materials include, but are not limited to, glass, fused silica, silicone rubber, silicon, ceramics, and polymeric substrates, e.g., plastics, depending on the intended application.

Technical benefits include the asymmetric flow profile due to the pillar arrays. The geometry of the pillar array (e.g. pitch, pillar size, lattice constants) determines to what extent a pillar array will be able to separate larger particles from smaller particles. Tuning the geometric parameters of the array allows a designed arrays that either can separate larger particles from smaller particles (these arrays are termed separators), or which distort all particle paths by causing an asymmetric flow, causing all particles to be pushed to one side of the array. These later arrays are termed condensers, as they have the effect to displace all particles and concentrate them on one side of a pillar array channel. Condensers can be used to focus particles into a narrow jet without the use of additional flow streams or pressure control, thus simplifying the design of fluidic systems. Concentration of particles allows (1) reducing the effects of diffusion, (2) formation of narrow jets which can then be fed into separators to achieve high resolution particle fractionation, all in a single channel, and (3) increases the concentration of a sample, which can be useful for rare or highly diluted particle solutions needed in a diagnostic. In one or more embodiments, the invention encompasses the idea of using different sets of arrays with different geometric parameters, in sequence or parallel, to generate "lensing" effects on particle streams, opening the possibility for manipulating particle flows by manipulating the structures through which the flows pass.

Additional technical benefits include utilizing a two stage approach that is advantageous because the separation efficiency depends on the cross-section of the particle jet. Diffusion ultimately limits the resolution of a separator array; the more narrow a particle jet injected into a separator, the more time (spatial extend) is available to separate the particle streams. By tuning the condenser, narrow particle jets can be made such that there is no overlap between the bumped (large particle) and zig zag mode (small particle) jets in the separator device, leading to high resolution and optimum performance. Using condenser geometry simplifies this jet formation process, allowing a smaller device footprint and thus larger scale integration (higher device density). The condenser has flexibility in terms of where the concentration can be formed; narrow jets can be focused to any position along the width of the channel by having two sets of pillar arrays, parallel to each other, with varied bumping directions.

Additional technical benefits include the combined effect of focusing an entire particle flux to the rights side of the array of pillars, effectively concentrating the first and second material to a narrow volume. The advantage to this is the ability to concentrate particles of all sizes into narrow stream of jet without having to use any additional input fluid or pressure. Current methods require stream focusing to generate this narrow stream which includes a concentrated particle jet which requires at least one or two additional input flows which require balancing of the pressures between the particle flow and the input flows. Therein lays a difficulty of scaling and controlling these multiple flows, especially for large scale, parallel device integration.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A deterministic lateral displacement array comprising:
   a channel, within a substrate, having a first sidewall, a second sidewall, and a channel length;
   a condenser portion comprising:
   an entry port and an exit port; and
   a first array of pillars disposed between the entry port and the exit port of the condenser portion along the channel length, the first array of pillars configured to drive a first material particle and a second material particle towards the first sidewall of the channel; and
   a separator portion comprising:
   an entry port and an exit port, the entry port of the separator portion arranged with the exit port of the condenser portion such that the first material particle and the second material particle flow from the exit port of the condenser portion into the entry port of the separator portion; and
   a second array of pillars disposed between the entry port and the exit port of the separator portion along the channel length, the second array of pillars configured to drive the first material particle towards the second sidewall of the channel.

2. The deterministic lateral displacement array of claim 1, wherein the first material particle has a first particle size and the second material particle has a second particle size, the first particle size is greater than the second material particle size.

3. The deterministic lateral displacement array of claim 1, wherein the first array of pillars comprises:
   a first pair of pillars and a second pair of pillars;
   the first pair of pillars comprises a first pillar and a second pillar;
   the second pair of pillars comprises a third pillar and a fourth pillar;
   the first pillar, the second pillar, the third pillar, and the fourth pillar have a first diameter of $D_0$ length;
   the first pillar has a central axis and the second pillar has a central axis, the central axis of the first pillar and the central axis of the second pillar define a first line having a length $D_y$ that is substantially perpendicular to the first sidewall;
   the third pillar has a central axis and the fourth pillar has a central axis, the central axis of the third pillar and the central axis of the fourth pillar define a second line having a length $D_y$ that is substantially perpendicular to the first sidewall;
   the central axis of the first pillar and the central axis of the third pillar are off-set by $\Delta$ distance in an off-set direction, the off-set direction is substantially perpendicular to the first sidewall; and
   the central axis of the second pillar and the central axis of the fourth pillar are off-set by $\Delta$ distance in the off-set direction.

4. The deterministic lateral displacement array of claim 1, wherein the second array of pillars comprises:
   a third pair of pillars and a fourth pair of pillars;
   the third pair of pillars comprises a fifth pillar and a sixth pillar;
   the fourth pair of pillars comprises a seventh pillar and an eighth pillar;
   the fourth pillar, the fifth pillar, the sixth pillar, and the seventh pillar have a second diameter of $D_0'$ length;
   the fifth pillar has a central axis and the sixth pillar has a central axis, the central axis of the fifth pillar and the central axis of the sixth pillar define a third line having a length $D_{y'}$ that is substantially perpendicular to the first sidewall;
   the seventh pillar has a central axis and the eighth pillar has a central axis, the central axis of the seventh pillar and the central axis of the eighth pillar define a fourth line having a length $D_y'$ that is substantially perpendicular to the first sidewall;
   the central axis of the fifth pillar and the central axis of the seventh pillar are off-set by $\Delta'$ distance in an off-set direction, the off-set direction is substantially perpendicular to the first sidewall; and
   the central axis of the sixth pillar and the central axis of the eighth pillar are off-set by $\Delta'$ distance in the off-set direction.

5. The deterministic lateral displacement array of claim 3, wherein the first material particle has a migration angle of $\theta_p$ in the condenser portion;
   the second material particle has a migration angle of $\theta$ in the condenser portion;
   wherein a degree of divergence of the first material particle and the second material particle in the condenser portion is defined by $\theta/\theta_p$;

the degree of divergence is a function of $D_0/D_y$; and the condenser portion includes a degree of divergence that tends to one as $D_0/D_y$ tends to one.

* * * * *